US006692963B1

(12) United States Patent
Bausher et al.

(10) Patent No.: US 6,692,963 B1
(45) Date of Patent: Feb. 17, 2004

(54) METHOD OF REPRODUCING PLANTS BY SOMATIC EMBRYOGENESIS

(75) Inventors: Michael Bausher, Fort Pierce, FL (US); Randall Niedz, Vero Beach, FL (US); Scott Hyndman, Vero Beach, FL (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 141 days.

(21) Appl. No.: 09/884,798

(22) Filed: Jun. 19, 2001

(51) Int. Cl.[7] .............................. C12N 5/00; C12N 5/02

(52) U.S. Cl. ....................................................... 435/422

(58) Field of Search ......................................... 435/422

(56) References Cited

U.S. PATENT DOCUMENTS

| | | |
|---|---|---|
| 5,034,326 A | 7/1991 | Pullman et al. |
| 5,036,007 A | 7/1991 | Gupta et al. |
| 5,041,382 A | 8/1991 | Gupta et al. |
| 5,236,841 A | 8/1993 | Gupta et al. |
| 5,294,549 A | 3/1994 | Pullman et al. |
| 5,482,857 A | 1/1996 | Gupta et al. |
| 5,506,136 A | 4/1996 | Bekwar et al. |
| 5,732,505 A | 3/1998 | Carlson et al. |
| 5,856,191 A | 1/1999 | Handley, III |
| 6,071,746 A | 6/2000 | Seabrook et al. |

OTHER PUBLICATIONS

Sorvari, S. et al., "The utilisation of an embryo breeder technique for maturation of somatic embryos," 1998, Acta Horticulturae, No. 461, pp. 445–450.*

Ranga Swamy, N.S., "Culture of Nuclear Tissue fo Citrus in vitro", *Experientia*, vol. 14, pp. 111–112, 1958.

Halperin, W., "In Vitro Embryogenesis: Some Historical Issues and Unresolved Problems", *In Vitro Embryogenesis in Plants*, p. 1, 1995.

Ammirato, P.V., "Embryogenesis", *Handbook of Plant Cell Culture*, vol. 1, (3), pp. 82–123, 1983.

Niedz, R., et al., "Analysis of Sweet Orange (Citrus sinensis (L.) Osbeck) Callus Cultures for Volatile Compounds by Gas Chromatography With Mass Selective Detector", *Plant Cell. Tissue and Organ Culture*, vol. 51, pp. 181–185, 1997.

Redenbaugh, K., "Introduction", *Synseeds Applications of Synthetic Seeds to Crop Improvement*, Chapter 1, pp. 1–3, 1993.

Sanada, Matsuyoshi, et al., "Celery and Lettuce", *Synseeds*, Chapter 17, pp. 305–309, 1993.

McKersie, B., et al., "Synthetic Seeds of Alfalfa", *Synseeds*, Chapter 14, pp. 231–233, 1993.

Klimaszewska, K., et al., "Influence of Gelling Agents on Culture Medium Gel Strength, Water Availability, Tissue Water Potential, and Maturation Response in Embryogenic Cultures of Pinus Strobus L.", *In Vitro Cell. Dev. Biol. Plant*, vol. 36, pp. 279–286, Jul.–Aug. 2000.

Debergh, P., et al., "Mass Propagation of Globe Artichoke (*Cynera scolymus*): Evaluation of Different Hypotheses to Overcome Vitrification with Special Reference to Water Potential", *Physiol. Plant.*, vol. 53 pp. 181–187, 1981.

Attree, S.M., et al., "Some Effects on Layers of Sodium Sulfate and Magnesium Sulfate in Their Drinking Water", *Annals of Botany*, vol. 68, pp. 519–525, 1991.

(List continued on next page.)

*Primary Examiner*—Bruce R. Campell
*Assistant Examiner*—Susan B. McCormick
(74) *Attorney, Agent, or Firm*—John D. Fado; G. Byron Stover

(57) ABSTRACT

A method has been discovered for reproducing plants by somatic embryogenesis by placing embryogenic tissue or organ onto a semi-permeable membrane that is on a culture medium and incubating to produce a normal somatic embryo.

13 Claims, 1 Drawing Sheet

OTHER PUBLICATIONS

Linossier, L., et al., "Effects of Abscisic Acid and High Concentrations of PEG on *Hevea brasiliensis* Somatic Embryos Development", *Plant Science*, vol. 124, pp. 183–191, 1997.

Svobodova, H., et al., "Somatic Ebmryogenesis in Norway Spruce: Anatomical Study of Embryo Deelopment and Influence of Polyethylene Glycol on Maturation Process", *Plant Physiol. Biochem.*, vol. 37, pp. 209–221, 1999.

Button, J., et al., "Fine Structure of and Embryoid Development from Embryogenic Ovular Callus of 'Shamouti' Orange (Citrus sinensis Osb.)", *J. Of Experimental Botany*, vol. 25, (85), pp. 446–457, Apr. 1974.

Rangan, T.S., et al., "In Vitro Initiation of Nucellar Embryos in Monoembryonic Citrus", *HortScience*, vol. 3, (4), pp. 226–227, Winter 1968.

Yantcheva, A., et al., "Direct Somatic Embryogenesis and Plant Regeneration of Carnation (*Dianthus caryophyllus* L.)", *Plant Cell Reports*, vol. 18, pp. 148–153, 1998.

Jain, S.M., et al., "Somatic Embryogenesis in Woody Plants", *Forestry Sciences*, vol. 1, pp. vi–x.

Shozo, K., A., et al., "Conditions for High Frequency Embryogenesis from Orange (Citrus sinensis Osb.) Protoplasts", *Plant Cell Tissue Oran. Culture*, vol. 4, pp. 249–259, 1985.

Murashige, T., et al., "Growth Factor Requirements of Citrus Tissue Culture", *Proceedings First Intern. Citrus Symposium*, vol. 3, pp. 1155–1161, 1969.

Von Aderkas, P., et al., "Influencing Micropropagation and Somatic Embryogenesis in Mature Trees by Manipulation of Phase Change, Stress and Culture Environment", *Tree Physiology*, vol. 20, pp. 921–928, 2000.

* cited by examiner

METHOD OF REPRODUCING PLANTS BY SOMATIC EMBRYOGENESIS

BACKGROUND OF THE INVENTION

The present invention relates to a method of reproducing plants by somatic embryogenesis involving placing embryogenic tissue onto a semi-permeable membrane which is on a culture medium and incubating to produce a normal somatic embryo.

Somatic embryogenesis has been widely demonstrated across the plant kingdom and includes angiosperm and gymnosperm, dicot and monocot, and herbaceous and woody plant species (Jain, S. M.; Gupta, P. K.; Newton, R. J. eds., Somatic embryogenesis in woody plants, vol. 1-history, molecular and biochemical aspects, and applications, Kluwer Academic Publishers, 1995; Thorpe, T. A., In vitro embryogenesis in plants, Kluwer Academic Publishers, 1995). The efficient production of somatic embryos is of considerable practical and biological interest compared to plants regenerated via organogenesis. Some of the prospective advantages of somatic embryogenesis include the following (Ammirato, P. V., Embryogenesis, In: Evans, E. A., Sharp, W. R., Ammirato, P. V., Yamada, Y., eds., Handbook of plant cell culture, Volume 1, Techniques for propagation and breeding, Macmillan Publishing Company, 1983:82–123): plant regeneration is more efficient since somatic embryos are bipolar structures and germination is a one-step process whereas organogenesis generally requires separate initiation of a shoot and root meristem; many more plants can be produced than is possible by organogenesis; somatic embryos can be encapsulated and treated like normal seed (i.e., stored and shipped); somatic embryos could be used for long-term storage in germplasm banks because of inherent dormancy properties; somatic embryos produce secondary metabolites not produced by undifferentiated callus (Niedz, R. P., et al., Plant Cell Tiss. Org. Cult., 51:181–185 (1997)); and somatic embryogenesis is a biological phenomenon uniquely suited as a tool to study basic questions of plant growth and development.

Citrus was one of the earliest plant genera where somatic embryogenesis was reported (Ranga Swamy, N. S., Experientia, 14:111–112 (1958); Maheshwari, P., and N. S. Ranga Swamy, Indian J. Hort., 15:275–282 (1958)). However, the routine production of large numbers of normal somatic embryos in alfalfa (McKersie, B. D., and Bowley, S. R., Synthetic seeds of alfalfa, In: Redenbaugh, K., eds., Synseeds: applications of synthetic seeds to crop improvement, CRC Press, 1993:231–256), carrot (Molle, F., et al., Carrot somatic embryogenesis and its application to synthetic seeds, In: Redenbaugh, K., eds., Synseeds: applications of synthetic seeds to crop improvement, CRC Press; 1993:257–287), or celery and lettuce (Sanada, M., et al., Celery and lettuce, In: Redenbaugh, K., eds. Synseeds: applications of synthetic seeds to crop improvement, CRC Press, 1993:305–327) is not possible for most species, including Citrus, where somatic embryogenesis has been reported. Globular stage embryos are readily produced from citrus embryogenic callus in large numbers. However, normalized development of these embryos has not been reported.

SUMMARY OF THE INVENTION

In accordance with the present invention there is provided a method of reproducing plants by somatic embryogenesis involving placing embryogenic tissue onto a semi-permeable membrane which is on a culture medium and incubating to produce a normal somatic embryo.

DETAILED DESCRIPTION OF THE INVENTION

Figure 1:
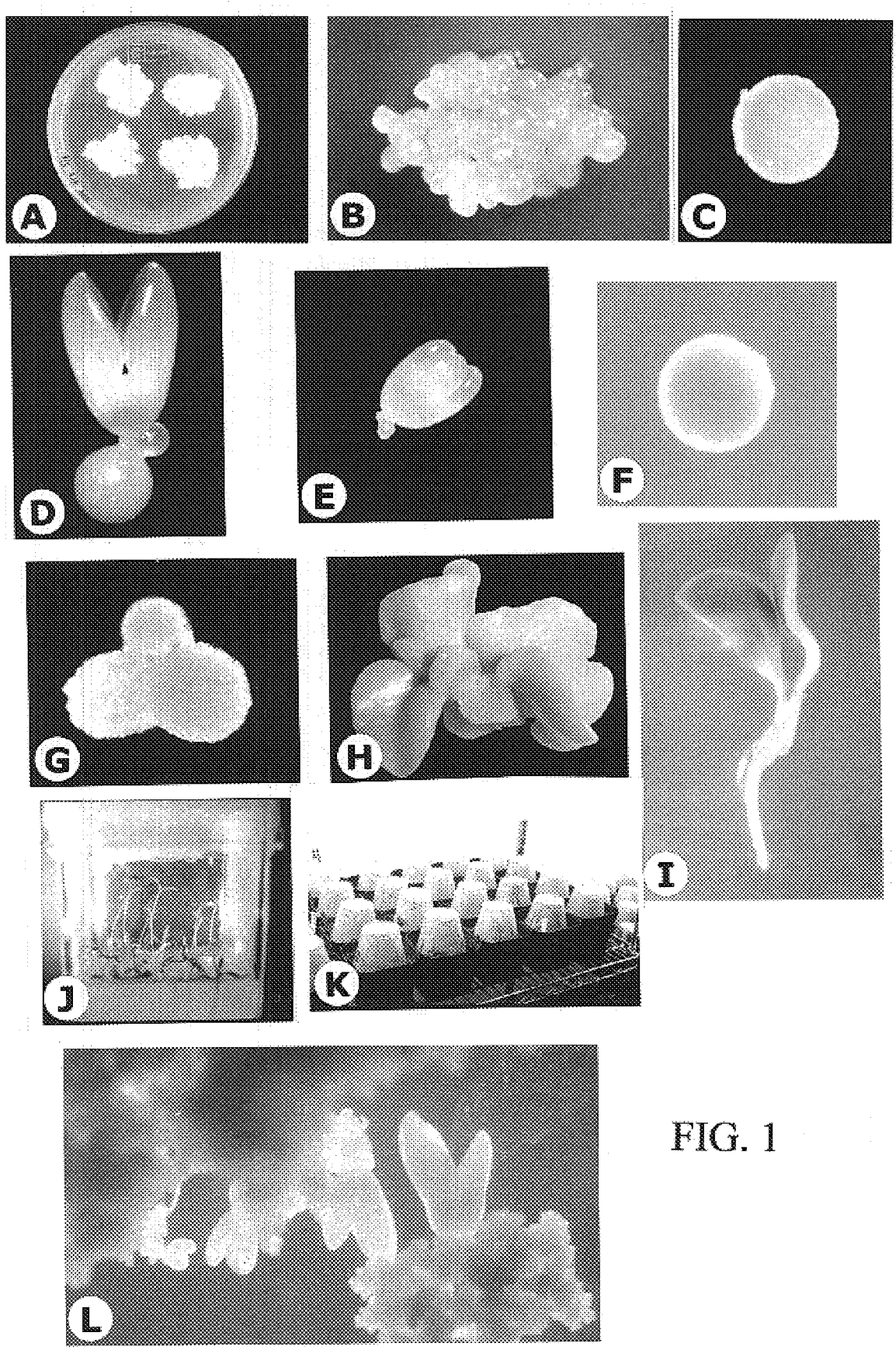
FIG. 1 shows the results of seven membrane treatments and four control treatments on embryogenesis: (A) embryogenic cell line H97 derived from *C. sinensis* cv. 'Hamlin;' (B) H97 globular embryos induced by culture on glycerol-based medium after six weeks; (C) an H97 globular embryo used in embryo development experiments; (D) heart-shaped (HS) type embryo developed on cellulose acetate membrane; (E) multiple cotyledons (MC) type embryo developed on cellulose acetate membrane; (F) nonresponsive (NR) type embryo; (G) multiple globular (MG) type embryo; (H) teratoma (TER) type embryo; (I) two week old plantlet obtained from germination of cellulose acetate membrane-derived HS embryo; (J) four week old plantlets obtained after germination of cellulose acetate membrane-derived HS embryos; (K) germinated plantlets in soil-less mix and covered with plastic cups in a growth chamber prior to movement to greenhouse; and (L) HS embryos developed directly from H97 embryogenic callus with no glycerol induction.

The present invention relates to a method of reproducing plants by somatic embryogenesis involving placing embryogenic tissue onto a semi-permeable membrane which is on a culture medium and incubating to produce a culture medium having thereon a normal somatic embryo.

Plants that may be reproduced by the present invention include any plant species that can be regenerated by the somatic embryogenic development pathway. Such species are initially determined by morphology with verification of somatic embryogenesis by histological confirmation of a bipolar structure; such species are easily determined by one skilled in the art, as shown in the examples below. Somatic embryogenesis has been documented in angiosperms and gymnosperms, dicots and monocots, and herbaceous and woody plant species. Generally, such plants include the seed plants of Ginkgophyta (Ginkgo), Cycadophyta (cycads), Coniferophyta (conifers), and Anthophyta (angiosperms), such as hardwood and conifer forest crops (e.g., pines, spruces, and firs) and citrus crops (e.g., Citrus species such as *C. sinensis*, especially 'Hamlin' and 'Valencia'). Included are woody gymnosperms of the order Coniferales, including species within the families Pinacae, Cupressacae, and Taxodiaceae, and species within the genera Abies, Pinus, Picea, Tsuga, Pseudotsuga, Thuja, Juniperus, Larix, Taxus and Sequoia. Other plants include, but are not limited to, the genera Elaeis, Phoenix, Eucalyptus, Quercus, Vitis, Malus, Triticum, Oryza, Glycine, Avena, Brassica, Saccharum, Hordeum, Fagopyrum, Gossypium, Beta, Arachis, Humulus, Iopomea, Musa, Manihot, Coffea, Camellia, Rosa, Coca, Canabis, Papaver, Carica, Cocos, Daucus, Medicago, Zea, Theobroma, Abies, Acer, Alnus, Arbutus, Asimina, Betula, Carpinus, Carya, Castanea, Celtis, Cercis, Chamaecyparis, Cornus, Cryptomeria, Eucalyptus, Fagus, Fraxinus, Gleditsia, Gymnocladus, Hamamelis, Juglans, Juniperus, Larix, Liriodendron, Magnolia, Malus, Morus, Nyssa, Ostrya, Picea, Pinus, Platanus, Populus, Prunus, Pseudotsuga, Pielea, Quercus, Rhamnus, Rhus, Salix, Sambucus, Sassafras, Sequoia, Sorbus, Taxus, Thuja, Tilia, Tsuga, Ulmus, and Viburnum.

The embryogenic tissue or organ that is placed onto a semi-permeable membrane is any plant tissue or organ capable of forming somatic embryos. An organ is a group of cells or tissues in a multicellular organism that perform a particular function; for example, plant organs include leaves, roots, stems, flowers, and fruit, also included are root tips, stem tips, shoot tips, leaf primordia, primordia or immature parts of flowers, and immature fruits. In plants where embryogenic tissue is used, the tissue is generally a mass (e.g., $\geq 1$ mm in diameter) of uniform cells that appear morphologically like a callus (the term that is commonly used in plant tissue culture is embryogenic callus; e.g., wound callus). A callus is simply a tissue mass of cells; FIG. 1A is a picture of what the citrus callus generally looks like. Embryogenic tissue or organs can also include the various stages of somatic embryogenesis such as globular, heart, torpedo, and cotyledonary stages. For example, in citrus, embryogenic callus or globular stage somatic embryos, as described below, can be used. Generally, single cells of embryogenic tissue will not be sufficient in the present invention.

Semi-permeable membranes used in the present invention generally have pores large enough to allow some molecules to pass through but too small to allow other molecules to pass. This term is generally used to refer to membranes that allow the free passage of solvent but discriminates by size on the passage of solutes (i.e., solutes beyond a certain size are excluded from passing through the membrane). For example, one of the semi-permeable membranes used in the citrus example below had a cutoff value of 6–8 kD (kD=kilodaltons); this means that any molecules larger than approximately 6–8 kD in molecular weight would not be able to pass through the membrane. The filter paper membranes used below have pores or holes so large that virtually everything present in the tissue culture medium passes through the filter paper; this type of membrane is not semi-permeable but rather permeable. Preferred semi-permeable membranes are made of regenerated cellulose (purified cellulose can be chemically converted to a soluble form, a solution of soluble cellulose can then be converted back or "regenerated" into cellulose in a variety of useful forms (e.g., fibers, sheets, membranes)), cellulose acetate, cellulose nitrate, cellulose esters, polysulfone, polycarbonate, polyethylene, polyolefin, polypropylene, or polyvinylidene fluoride; more preferred semi-permeable membranes are made of regenerated cellulose or cellulose acetate; most preferred semi-permeable membranes are made of cellulose acetate. The embryogenic tissue must be in contact with the semi-permeable membrane in order for normal embryos to develop; the membrane is then placed on top of the culture medium or the membrane is already on top of the culture medium.

The semi-permeable membrane is generally on top of a culture medium (which is usually in a container that allows gas exchange but prevents the introduction of microorganisms, generally the container will be a petri dish). The culture medium may be any medium containing nutrients, carbon sources, organic compounds, or growth regulators typically used in in vitro culture of plants; for example, such culture medium may be a gelled medium such as Murashige and Tucker's (MT) basal medium (described below). Generally, the container is sealed (e.g., using elastic tape such as Parafilm) after placing embryogenic tissue or organs onto the semi-permeable membrane.

The embryogenic tissue may be placed on the semi-permeable membrane which is already on top of the culture medium or the embryogenic tissue may be placed on the semi-permeable membrane which is then placed on top of the culture medium. The embryogenic tissue must be in direct contact (fully or partially) with the semi-permeable membrane.

After the embryogenic tissue has been placed on the semi-permeable membrane, the embryogenic tissue is incubated until a normal embryo develops. Incubation conditions (e.g., temperature, time, and photoperiod) are easily determined by one skilled in the art. For citrus, the embryos generally appear after about 6 weeks of incubation at about 27° C. with about a 4-hour photoperiod where the light is provided by cool-white fluorescent tubes and the light intensity is between about 15-about 30 (e.g., 15–30) microEinsteins ($\mu Em^{-2}s^{-1}$).

The normal somatic embryo produced by the present invention is an embryo (i.e., a somatic embryo from tissue or organ in in vitro culture) capable of germination or a developmental stage of somatic embryogenesis leading to the development of a somatic embryo capable of germination. The term "embryo" by itself denotes an embryo derived from a zygote (i.e., the product of fusion of the germ cells-egg and sperm). In tissue culture, because the embryos are generally derived from somatic cells, they are thus distinguished by the term "somatic embryo."

Generally, after the normal somatic embryo has been produced, it is transferred to a culture medium (a second culture medium) and incubated to produce a culture medium having thereon a germinated somatic embryo. With some plant somatic embryos additional transfers (e.g., third, fourth) may be necessary for normal somatic embryo development, though some plant somatic embryos will not require transfer to a second medium. If additional transfers are required for normal development of the somatic embryos, the media may or may not be of the same kind of medium as the first culture medium (e.g., MT basal medium). The additional culture media may be composed of any support (e.g., gels, soils, soil-less mixes, foams, inert materials, etc.) and nutrients, carbon source, organic compounds, and growth regulators capable of allowing the normal somatic embryo to develop or germinate; thus the additional culture media may include in vitro or ex vitro culture. Generally, the somatic embryo is germinated in vitro and the resulting plantlet is transferred and grown ex vitro (i.e., transferred to a support such as soil or soil-less mix).

The following examples are intended only to further illustrate the invention and are not intended to limit the scope of the invention as defined by the claims.

EXAMPLES

Materials and Methods

Plant material and culture medium: An embryogenic callus line (H97) was initiated from the ovules of *Citrus sinensis* (L.) Osbeck cv. 'Hamlin' as described by Kobayashi et al. (Plant Cell Tissue Organ Culture, 4: 249–259 (1985)). H97 was maintained on Murashige and Tucker's (MT) basal medium (Murashige, T., and D. P. H. Tucker, Proceedings 1$^{st}$ Internal. Citrus Symp., Univ. of California-Riverside, 3: 1155–1161 (1969)) at 27° C., 15–20 $\mu Em^{-2}s^{-1}$, 4-h photoperiod provided by cool-white fluorescent lamps, and a 28-day subculture cycle. Plant material used included both H97 embryogenic callus and glycerol-induced globular embryos. Glycerol-induced embryogenesis was initiated by subculturing H97 onto MT basal medium where sucrose was replaced by 2% (v/v) glycerol as the primary carbon source. Globular-stage embryos formed on the glycerol induction medium were used in further embryo development experiments. All culture media were autoclave-sterilized for 15 min at 103 kPa and 121° C.

Experiment 1—Membranes tested: H97 glycerol-induced globular embryos were cultured on various membranes overlaid on the MT basal medium used to maintain H97; culture conditions were 27° C., 15–20 $\mu Em^{-2}s^{-1}$, 4-h photoperiod provided by cool-white fluorescent lamps. The following seven membranes were tested: Spectra/Por 6 k–8 k MW cutoff cellulose acetate (Spectrum Companies, Gardena, Calif.), Gelwrap >400,000 k MW cutoff cellulose acetate (Biodesigns, Carmel, N.Y.), nitrocellulose, Immobilon-P polyvinylidene fluoride (Millipore, Bedford, Mass.), cellulose filter paper (Whatman, Cliffton, N.J.), positively charged nylon and neutral charge nylon (Amersham Life Science, Piscataway, N.J.). The control treatment included agar only (i.e., no membrane). A follow-up experiment with three treatments was also conducted to include cutting the Spectra/Por membrane into 3–5 mm pieces and incorporating the membrane pieces directly into the culture medium, Spectra/Por membrane overlaid onto MT basal medium supplemented with 185 mg $l^{-1}$ adenine sulfate+500 mg $l^{-1}$ malt extract, MT basal medium supplemented with 185 mg $l^{-1}$ adenine sulfate+500 mg $l^{-1}$ malt extract with no membrane, and the MT basal medium only control.

Experiment 2—Polyethylene glycol in the culture medium: PEG-3350 (Sigma, St. Louis, Mo.) was added to the MT basal medium at 0, 2.5%, 5%, 10%, or 15% (w/v). The culture medium was solidified with 0.3 g $l^{-1}$ Gelrite (Sigma, St. Louis, Mo.). H97 callus or glycerol-induced globular embryos were cultured onto the PEG supplemented media or MT basal medium as a control. Culture conditions were 27° C., 15–30 $\mu Em^{-2}s^{-1}$, 4-h photoperiod provided by cool-white fluorescent lamps.

Experiment 3—Gelling agents in the culture medium: Two gelling agents were added to MT basal culture medium at various concentrations; bacteriological agar (USB, Cleveland, Ohio) at 0.8, 1, 2, or 3% (w/v), or Gelrite at 0.15, 0.3, 0.6, or 0.9% (w/v). H97 callus or glycerol-induced globular embryos were cultured onto the gel modified media or MT basal medium as a control. Culture conditions were 27° C., 15–30 $\mu Em^{-2}s^{-1}$, 4-h photoperiod provided by cool-white fluorescent lamps.

Embryo germination: Heart-shaped embryos obtained from the membrane treatments were germinated (at 27° C., 15–20 $\mu Em^{-2}s^{-1}$, 16-h photoperiod provided by cool-white fluorescent lamps) on MT basal culture medium with 0.5% (w/v) sucrose and 1 $\mu$M GA in Magenta containers (Magenta Corp, Chicago, Ill., USA). Germinated embryos were planted into a soil-less potting mix, covered with a plastic cup, and acclimated for four weeks in a growth chamber (25° C., 80 $\mu Em^{-1}s^{-1}$, 16-h photoperiod) before moving the plants to the greenhouse.

Experimental design and data analysis: Each treatment included both H97 embryogenic callus and glycerol-induced globular embryos. For H97 callus, each treatment included 3 g of callus per culture dish, spread evenly over the surface of the gelled medium or membrane. For glycerol-induced embryos, each treatment included sixteen globular embryos arrayed in a 4×4 array per dish. Each treatment included five 60×15 mm polystyrene culture dishes sealed with Parafilm and was repeated once. Embryo development was recorded 6 weeks after culture. The development of each embryo was classified into one of five categories—heart-shaped (HS), multiple cotyledon (MC), nonresponsive (NR), multiple globular (MG), or teratoma (TER). Analysis of nonzero classes was conducted using a contingency table analyzed by chi-square.

Results and Discussion

Experiment 1—Membranes tested: This experiment included seven membrane treatments and four control treatments. Source tissue, embryo types, and plant regeneration from heart-shaped embryos produced on cellulose acetate membranes in FIG. 1: (A) Embryogenic cell line H97 derived from C. sinensis cv. 'Hamlin.' (B) H97 globular embryos induced by culture on glycerol-based medium after six weeks. (C) An H97 globular embryo used in embryo development experiments. (D) Heart-shaped (HS) type embryo developed on cellulose acetate membrane. (E) Multiple cotyledons (MC) type embryo developed on cellulose acetate membrane. (F) Nonresponsive (NR) type embryo. (G) Multiple globular (MG) type embryo. (H) Teratoma (TER) type embryo. (I) Two week old plantlet obtained from germination of cellulose acetate membrane-derived HS embryo. (J) Four week old plantlets obtained after germination of cellulose acetate membrane-derived HS embryos. (K) Germinated plantlets in soil-less mix and covered with plastic cups in a growth chamber prior to movement to greenhouse.

The effect of the membrane treatments on embryogenesis was evaluated using both embryogenic callus (FIG. 1A) and globular-stage embryos initiated from embryogenic callus by glycerol induction. Embryogenic callus cultured on glycerol induction medium will completely develop into globular embryos within 5–6 weeks with no remaining callus (FIG. 1B). Further development of normal HS embryos does not occur with continued culture on glycerol medium. The resulting embryo morphologies of the individually cultured globular embryos (FIG. 1C) for each treatment after six weeks of culture are listed in Table 1, and a representative embryo of each morphology class is presented in FIGS. 1D–1H. The data presented in Table 1 represents the mean of 2 experiments. A simple presentation of means is the clearest manner to present the results of this experiment because the many zero classes make statistical analysis of the overall experiment difficult.

TABLE 1

EFFECT OF MEMBRANE TYPE ON GLYCEROL-INDUCED GLOBULAR EMBRYO DEVELOPMENT AND MORPHOLOGY AFTER 6 WEEKS[a]

| Membrane Treatments[b] | Embryo Morphology[c] | | | | |
|---|---|---|---|---|---|
| | HS | MC | NR | MG | TER |
| 1) No membrane-MT basal medium | 0 | 0 | 20 | 35 | 26 |
| 2) No membrane-MT basal medium + 500 mg $l^{-1}$ malt extract | 0 | 0 | 13 | 40 | 28 |
| 3) Cellulose acetate-6k–8k MW cutoff | 15 | 21 | 28 | 17 | 0 |
| 4) Cellulose acetate-6k–8k MW cutoff-MT basal medium + 500 mg $l^{-1}$ malt extract | 18 | 22 | 22 | 19 | 0 |
| 5) Cellulose acetate- >400,000k MW cutoff | 9 | 14 | 42 | 17 | 0 |
| 6) Nitrocellulose | 0 | 0 | 9 | 27 | 44 |
| 7) PVDF | 0 | 0 | 80 | 0 | 0 |
| 8) Cellulose filter paper | 0 | 0 | 13 | 32 | 36 |
| 9) Nylon-positive charge | 0 | 0 | 11 | 29 | 41 |

TABLE 1-continued

EFFECT OF MEMBRANE TYPE ON GLYCEROL-INDUCED
GLOBULAR EMBRYO DEVELOPMENT AND MORPHOLOGY
AFTER 6 WEEKS[a]

| Membrane Treatments[b] | Embryo Morphology[c] | | | | |
|---|---|---|---|---|---|
| | HS | MC | NR | MG | TER |
| 10) Nylon-neutral charge | 0 | 0 | 12 | 20 | 49 |
| 11) Cellulose acetate-6k–8k MW cutoff-chopped | 0 | 0 | 13 | 40 | 27 |

[a]Data (rounded up) represents treatment means from 2 experiments where each treatment was composed of 5 plates with 16 globular embryos/plate.
[b]Cellulose acetate 6k–8k MW cutoff (Spectra/Por); Cellulose acetate > 400,000k MW cutoff (Gelwrap)
[c]HS = heart-shaped; MC = multiple cotyledon; NR = nonresponsive; MG = multiglobular; TER = teratoma Of particular interest was the formation of normal heart-shaped embryos, as this represents the next normal developmental stage after the globular form. The other morphologies are representative of varying degrees of abnormal or nonresponsive development. Referring to Table 1, normal heart-shaped embryos (FIG. 1D) were only formed on the three cellulose acetate membrane treatments (#3, #4, and #5). No normal heart-shaped embryos were formed on the nitrocellulose (#6), PVDF (#7), cellulose (#8), nylon (#9 & #10) membrane treatments, three of the four control treatments (#1, #2, or #11). Heart-shaped embryos were formed on control treatment #4; #4 was the same as #3 (i.e., included cellulose acetate) but utilized a MT basal medium+500 mg $1^{-1}$ malt extract, a medium reported to initiate embryogenesis in citrus (Rangan, T. S., et al., HortScience, 3: 226–227 (1968)). To compare the two types of cellulose acetate membranes (#3 and #5), a 2×2 contingency table was constructed with the two treatments, #3 and #5, assigned to row 1 and 2, respectively, and heart-shaped or non-heart-shaped embryo morphologies assigned to column 1 and 2, respectively. The non-heart-shaped classification was constructed by combining the data from all the non-heart-shaped categories (i.e., MC, NR, MG, and TER). The resulting analysis produced a chi-square of 1.765 with a $p \leq 0.1840$, indicating no significant difference in the number of HS embryos produced on either of the two cellulose acetate membranes.

HS embryos that developed on the cellulose acetate membranes were removed and germinated on basal medium where the sucrose concentration was reduced to 0.5%, and GA was included to promote shoot elongation. Shoot and root development proceeded rapidly (FIGS. 1I and 1J) and was ready for movement to the growth chamber after four weeks. Covering each pot with a plastic cup and gradually lifting the cup over a period of four weeks acclimatized the plantlets. Acclimatized plantlets were then moved to the greenhouse.

The MC embryo morphology (FIG. 1E) was similar to the HS morphology. MC embryos generally had three cotyledons rather than the two cotyledons of the normal HS morphology. Though MC embryos are abnormal, they are the closest morphologically to HS of all the abnormal morphologies. Like the HS results, the development of MC embryos occurred only on the three cellulose acetate membrane treatments. An analysis comparable to that listed above for the HS morphology using a 2×2 contingency table and was performed. The resulting analysis produced a chi-square of 1.792 with a $p \leq 0.1807$, indicating no significant difference in the number of MC embryos produced on either of the two cellulose acetate membranes.

The TER embryo morphology (FIG. 1H) is the most diverse classification. It represents any morphology that cannot be classified into the other categories. The morphology is generally characterized by extensive growth of multiple and abnormal cotyledon-like structures. Again, referring to Table 1, TER morphologies were not observed on the cellulose acetate treatments (#3, #4, #5) or the PVDF treatment (#7). All embryo development on the PVDF membrane was of the NR morphology. PVDF membranes are hydrophobic and the NR classification was probably due to a rapid drying out of the membrane and subsequent death of the embryos. The membrane treatments with TER morphologies (#6, #8, #9, #10) were compared to the three nonmembrane control treatments (#1, #2, #11) by a chi-square "goodness of fit" test. The resulting analysis produced a chi-square of 11.41 with a probability $\leq 0.0007$ indicating a highly significant relationship between the development of the TER morphology on these membranes.

To determine whether the normalizing effect of the cellulose acetate membrane was due to the release of a chemical constituent from the membrane, a control treatment was included in which pieces of autoclaved Spectra/Por membrane were added into the warm liquid medium prior to cooling and solidification. No heart-shaped embryos were observed to form, indicating that the effect is not the result of a released chemical from the membrane.

Experiment 2—Polyethylene glycol in the culture medium: To investigate water stress as a possible mechanism for the normalized transition of globular to heart-shaped embryos observed on the cellulose acetate membranes, PEG was incorporated into the culture medium at various concentrations. The total water potential of a culture system can dramatically alter the growth and development of plant tissues and organs. Total water potential in plant tissue culture systems is primarily a function of two components, osmotic and matric potentials; the pressure potential is not a function of semi-solid (e.g., agar) tissue culture media (Debergh, P., et al., Physiol. Plant., 53:181–187 (1981)). The addition of PEG to culture medium lowers the osmotic potential of the medium.

Glycerol-induced globular embryos were placed onto culture medium supplemented with PEG. Gelrite was used as a gelling agent as it was difficult to achieve adequate gelling of agar with PEG concentrations greater than 5% (w/v). No heart-shaped or multiple cotyledon embryos were observed to develop from the cultured globular embryos after six weeks. These results suggest that the normalized development observed on the cellulose acetate membranes cannot be equated with the normalized development that PEG induces in some plant embryogenic systems such as Hevea brasiliensis (Linossier, L., et al., Plant Sci., 124:183–191 (1997)), Picea species (Svobodova, H., et al., Plant Physiol. Biochem., 37:209–221 (1999); Attree, S. M., et al., Ann. Bot., 68:519–525 (1991)), and *Dianthus caryophyllus L.* (Yantcheva, A., et al., Plant Cell Rep, 18:148–153 (1998)). If water stress of the globular embryos on the cellulose acetate membranes is the primary mechanism of normalized development, it was not duplicated or approximated using PEG over a broad concentration range.

Experiment 3—Gelling agents in the culture medium: To investigate water stress induced by lowering the matric potential, glycerol-induced globular embryos were placed onto media with varying concentrations of agar (0.8 to 3%) or Gelrite (0.15–0.9%). Matric potential is primarily a function of the gelling agent concentration (Debergh, P., et al., Physiol. Plant., 53:181–187 (1981)). No heart-shaped or multiple cotyledon embryos were observed to develop from the cultured globular embryos after six weeks. These results suggest that the normalized development observed on the cellulose acetate membranes cannot be equated with the normalized development that occurs in some plant embryogenic systems such as Pinus strobus (Klimaszewska, K., In Vitro Cell. Dev. Biol. Plant, 36:279–286 (2000)) by reducing the matric potential by limiting water via increasing the gel concentration.

Development of citrus somatic embryos initiated from embryogenic callus generally results in abnormal morphologies during growth and development. Shoots can be regenerated by organogenesis from these abnormal structures, excised and rooted to recover plants. To normalize development, glycerol-induced globular stage somatic embryos of sweet orange (C. sinensis (L.) Osbeck cv. 'Hamlin') were cultured on 6 k–8 k MW cutoff cellulose acetate, >400,000 k MW cutoff cellulose acetate, nitrocellulose, polyvinylidene fluoride (PVDF), cellulose filter paper, positively charged nylon, or neutrally charged nylon membranes. Only globular stage embryos cultured on semi-permeable cellulose acetate membranes developed normal, 2-cotyledon, bipolar, heart-shaped embryos, and did not develop any aberrant teratoma-like structures. Heart-shaped embryos were developed and germinated on MT +0.5% sucrose+1 $\mu$M GA over a four week time and then transferred to a soil-less mix. Culture of embryogenic callus directly onto cellulose membranes resulted in the development of normal heart-shaped embryos indicating that glycerol induction of globular stage embryos is not necessary. Heart-shaped embryos were not observed when the osmotic potential of the medium was increased by the addition of 2.5% to 15% PEG; neither were they observed when the matric potential of the medium was increased by increasing the gelling agent concentrations of agar and Gelrite from 0.8% to 3% and 0.15% to 0.9%, respectively.

Thus the present study showed that semi-permeable membranes normalize the in vitro conversion of citrus globular stage embryos into normal heart-shaped stage somatic embryos capable of germination into complete plants. It is expected that similar results will be found with the use of other plants.

All of the references cited herein are incorporated by reference in their entirety. Also incorporated by reference in their entirety are the following U.S. Pat. Nos: 6,071,746; 5,856,191; 5,732,505; 5,482,857; 5,294,549; 5,236,841; 5,041,382; 5,036,007; and 5,034,326.

Thus, in view of the above, the present invention concerns (in part) the following:

A method of reproducing plants by somatic embryogenesis involving placing embryogenic tissue or organ onto a semi-permeable membrane (wherein the membrane is on a culture medium in a container or the membrane is placed on a culture medium in a container after the embryogenic tissue is placed on the membrane) and incubating at a time, temperature and photoperiod effective to produce a normal somatic embryo.

The above method wherein the plants are members of the genera Abies, Pinus, Picea, Tsuga, Pseudotsuga, Thuja, Juniperus, Larix, Taxus, Sequoia, or Citrus.

The above method wherein the plants are members of the Citrus genus.

The above method wherein the plants are members of Citrus sinensis.

The above method wherein the plants are members of Citrus sinensis (L.) Osbeck cv. 'Hamlin' or 'Valencia.'

The above method wherein the semi-permeable membrane is composed of regenerated cellulose, cellulose acetate, cellulose nitrate, cellulose esters, polysulfone, polycarbonate, polyethylene, polyolefin, polypropylene, polyvinylidene fluoride, or mixtures thereof.

The above method wherein the semi-permeable membrane is composed of regenerated cellulose, cellulose acetate, cellulose nitrate, or mixtures thereof.

The above method wherein the semi-permeable membrane is composed of cellulose acetate.

The above method further involving transferring the normal somatic embryo to a culture medium and incubating to produce a germinated embryo. And further involving removing the germinated embryo and planting in soil.

The method further involving incubating the normal somatic embryo to produce a germinated embryo. And further involving removing the germinated embryo and planting in soil.

The above method further involving sealing the container after placing embryogenic tissue onto a semi-permeable membrane.

The above method wherein the incubating is for about 6 weeks at about 27° C. with about a 4-hour photoperiod wherein the light is provided by cool-white fluorescent tubes and the light intensity is between about 15 to about 30 microEinsteins ($\mu$Em$^{-2}$s$^{-1}$).

A method of inducing or normalizing the development of normal plant somatic embryos, said method comprising placing embryogenic tissue onto a semi-permeable membrane, wherein said membrane is on a culture medium in a container or said membrane is placed on a culture medium in a container after said embryogenic tissue is placed on said membrane; and incubating at a time, temperature and photoperiod effective to produce a normal somatic embryo.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A method of reproducing plants by somatic embryogenesis, said method comprising placing embryogenic tissue or organ onto a semi-permeable membrane, wherein said membrane is on a culture medium in a container or said membrane is placed on a culture medium in a container after said embryogenic tissue is placed on said membrane; and incubating at a time, temperature and photoperiod effective to produce a normal somatic embryo, wherein said plants are members of the genera Abies, Pinus, Picea, Tsuga, Pseudotsuga, Thuja, Juniperus, Larix, Taxus, Sequoia, or Citrus; wherein said culture medium is a gelled medium.

2. The method according to claim 1, wherein said plants are members of the Citrus genus.

3. The method according to claim 1, wherein said plants are members of Citrus sinensis.

4. The method according to claim 1, wherein said plants are members of Citrus sinensis (L.) Osbeck cv. 'Hamlin' or 'Valencia.'

5. The method according to claim 1, wherein said semi-permeable membrane is composed of regenerated cellulose, cellulose acetate, cellulose esters, cellulose nitrate, polysulfone, polycarbonate, polyethylene, polyolefin, polypropylene, polyvinylidene fluoride, or mixtures thereof.

6. The method according to claim 1, wherein said semi-permeable membrane is composed of regenerated cellulose, cellulose acetate, cellulose esters, cellulose nitrate, or mixtures thereof.

7. The method according to claim 1, wherein said semi-permeable membrane is composed of cellulose acetate.

8. The method according to claim 1, further comprising transferring said normal somatic embryo to a culture medium and incubating to produce a germinated embryo.

9. The method according to claim 8, further comprising removing said germinated embryo and planting in soil.

10. The method according to claim 1, further comprising incubating said normal somatic embryo to produce a germinated embryo.

11. The method according to claim 10, further comprising removing said germinated embryo and planting in soil.

12. The method according to claim 1, further comprising sealing said container after said placing embryogenic tissue onto a semi-permeable membrane.

13. The method according to claim 12, wherein said incubating is for about 6 weeks at about 27° C. with about a 4-hour photoperiod wherein the light is provided by cool-white fluorescent tubes and the light intensity is between about 15 to about 20 $\mu Em^{-2}s^{-1}$.

* * * * *